United States Patent [19]

Eidenschink et al.

[11] 4,419,264
[45] Dec. 6, 1983

[54] FLUORINE-CONTAINING 4,4′-BIS-(CYCLOHEXYL)-BIPHENYL DERIVATIVES, AND DIELECTRICS AND ELECTRO-OPTICAL DISPLAY ELEMENTS CONTAINING THEM

[75] Inventors: Rudolf Eidenschink, Dieburg; Michael Römer, Rodgau; Ludwig Pohl, Darmstadt, all of Fed. Rep. of Germany

[73] Assignee: Merck Patent Gesellschaft mit beschränkter Haftung, Darmstadt, Fed. Rep. of Germany

[21] Appl. No.: 373,454

[22] Filed: Apr. 30, 1982

[30] Foreign Application Priority Data

Apr. 30, 1981 [DE] Fed. Rep. of Germany ....... 3117152

[51] Int. Cl.³ .................. G02F 1/133; C09K 3/34; C07C 25/18; C07C 43/184; C07C 43/142
[52] U.S. Cl. .................... 252/299.63; 252/299.5; 350/350 R; 568/660; 568/661; 570/129
[58] Field of Search ............ 252/299.5, 299.63; 350/350; 570/129; 568/660, 661

[56] References Cited

U.S. PATENT DOCUMENTS

| | | | |
|---|---|---|---|
| 4,330,426 | 5/1982 | Eidenschink et al. | 252/299.63 |
| 4,331,552 | 5/1982 | Eidenschink et al. | 252/299.63 |
| 4,368,135 | 1/1983 | Osman | 252/299.63 |

FOREIGN PATENT DOCUMENTS

| | | | |
|---|---|---|---|
| 19665 | 12/1980 | Europen Pat. Off. | 252/299.63 |
| 51738 | 5/1982 | European Pat. Off. | 252/299.63 |
| 62470 | 10/1982 | European Pat. Off. | 252/299.63 |
| 2939782 | 4/1981 | Fed. Rep. of Germany | 252/299.63 |
| 3139130 | 5/1982 | Fed. Rep. of Germany | 252/299.63 |
| 57-49688 | 3/1982 | Japan | 252/299.63 |
| 57-159730 | 10/1982 | Japan | 252/299.63 |
| 57-165326 | 10/1982 | Japan | 252/299.63 |
| 2039937 | 8/1980 | United Kingdom | 252/299.66 |
| 2086385 | 5/1982 | United Kingdom | 252/299.63 |

OTHER PUBLICATIONS

Gray, G. W., et al., Mol. Cryst. Liq. Cryst., vol. 67, No. 1-4, pp. 1-24 (1981).
Gray, G. W., et al., Mol. Cryst. Liq. Cryst., vol. 63, pp. 3-18 (1981).

*Primary Examiner*—Teddy S. Gron
*Attorney, Agent, or Firm*—Millen & White

[57] ABSTRACT

Compounds of the formula

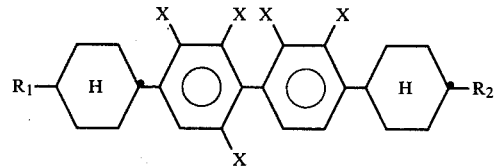

wherein $R_1$ and $R_2$ are identical or different and each is alkyl or alkoxy each of up to 8 C atoms, and one or two of the substituents X are fluorine and the others are hydrogen are valuable liquid crystalline materials.

10 Claims, No Drawings

FLUORINE-CONTAINING 4,4'-BIS-(CYCLOHEXYL)-BIPHENYL DERIVATIVES, AND DIELECTRICS AND ELECTRO-OPTICAL DISPLAY ELEMENTS CONTAINING THEM

BACKGROUND OF THE INVENTION

The properties of nematic or nematic-cholesteric liquid-crystalline materials whereby they significantly vary their optical properties, such as light absorption, light scattering, birefringence, reflectivity or color, under the influence of electric fields, are widely utilized for electro-optical display elements. The functioning of display elements of this type is based, for example, on the phenomena of dynamic scattering, the deformation of aligned phases, the Schadt-Helfrich effect in the twisted cell or the cholesteric-nematic phase transition.

For the industrial application of these effects in electronic components, liquid-crystalline dielectrics are required which must meet a large number of demands. Chemical resistance to moisture, air and physical influences, such as heat, radiation in the infrared, visible and ultraviolet regions, and continuous and alternating electric fields, is of particular importance. Industrially usable liquid-crystalline dielectrics are also required to have a liquid-crystalline mesophase in the temperature range from at least +10° C. to +50° C., preferably from 0° C. to 60° C., and the lowest possible viscosity at room temperature, which preferably should not exceed $70 \times 10^{-3}$ Pa.s. Finally, they must not have any characteristic absorption in the region of visible light, i.e., they must be colorless.

A number of liquid-crystalline compounds have already been disclosed, which fulfill the stability demands made on dielectrics for use in electronic components, and which are also colorless. These include, in particular, the p,p'-disubstituted phenyl benzoates described in German Offenlegungsschrift No. 2,139,628 and the p,p'-disubstituted phenylcyclohexane derivatives described in German Offenlegungsschrift No. 2,636,684. In both classes of compounds, and also in other known series of compounds with a liquid-crystalline mesophase, there are no individual compounds which form a liquid-crystalline nematic mesophase in the required temperature range of 10° C. to 60° C. Therefore, mixtures of two or more compounds are generally prepared in order to obtain substances which can be used as liquid-crystalline dielectrics. For this purpose, at least one compound having a low melting point and clear point is usually mixed with another compound having a markedly higher melting point and clear point. This normally gives a mixture, the melting point of which is below that of the lower-melting component, while the clear point is between the clear points of the components. Nevertheless, difficulties arise again and again in the preparation of optimum dielectrics, because the components having the high melting points and clear points frequently also impart a high viscosity to the mixtures. As a result, the switching times of the electrooptical display elements produced with these mixtures are extended in a undesirable manner. Moreover, problems are frequently caused by the fact that the mutual solubility of the various components, in particular at room temperature or lower temperatures, is only very limited.

SUMMARY OF THE INVENTION

Accordingly, it is an object of this invention to provide liquid-crystalline dielectrics which have a nematic phase within the required temperature range and, when used in liquid crystal cells, enable switching times which are sufficiently short at room temperature.

Upon further study of the specification and appended claims, further objects and advantages of this invention will become apparent to those skilled in the art.

These objects have been attained by providing 4,4'-bis-(cyclohexyl)-biphenyl derivatives of formula (I)

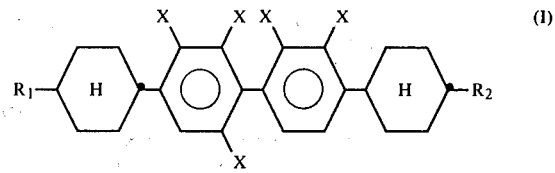

wherein $R_1$ and $R_2$, which are identical or different, are alkyl or alkoxy each of up to 8 C atoms, and one or two of the substituents X are fluorine and the others are hydrogen.

These compounds are outstandingly suitable for use as components of liquid-crystalline dielectrics. Additionally, they have an extremely wide range of application.

Depending on the selection of the substituents, the compounds of formula (I) can be used either as base materials representing the predominant part of liquid-crystalline dielectrics, or they can be added in smaller proportions of, for example, 2 to 45 percent by weight to liquid-crystalline base materials from other classes of compounds, in order to prepare dielectrics having a widened liquid-crystalline mesophase or to influence the magnitude of the dielectric anisotropy of such a dielectric.

By a suitable selection of the substituents $R_1$ and $R_2$, and the position or positions of the fluorine atoms, the compounds of formula (I) can be used either to prepare dielectrics having a positive dielectric anisotropy, for use in display elements based on the twisted nematic cell or on the cholesteric-nematic phase transition, or to prepare dielectrics having a dielectric anisotropy which only slightly differs from zero or is even negative, the latter dielectrics being used in display elements based on dynamic scattering or on the deformation of aligned phases (DAP effect).

In the pure state, the compounds of formula (I) are colorless, and they form nematic mesophases of low viscosity in a temperature range which is astonishingly wide and is favorable for electro-optical application.

The present invention thus relates to the 4,4'-bis-(cyclohexyl)-biphenyl derivatives of formula (I) and to their use as components of liquid-crystalline dielectrics. Moreover, the invention relates to liquid-crystalline dielectrics containing at least one 4,4'-bis-(cyclohexyl)-biphenyl derivative of formula (I), and to electro-optical display elements based on a liquid crystal cell which contains a liquid-crystalline dielectric of this type.

DETAILED DISCUSSION

In the 4,4'-bis-(cyclohexyl)-biphenyl derivatives of formula (I), the biphenyl portion is substituted by one or two fluorine atoms. If the molecule contains only one fluorine atom, those compounds of formula (Ia) are preferred in which the fluorine atom is in an ortho-position relative to the bond between the two phenyl rings.

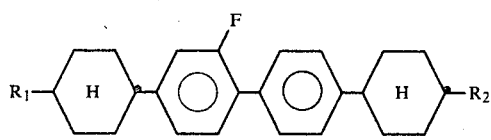

If the compounds of formula (I) contain two fluorine atoms, preferred among these are those in which the fluorine atoms are in ortho-positions relative to the bond between the two phenyl rings, i.e., compounds of formula (Ib) and (Ic):

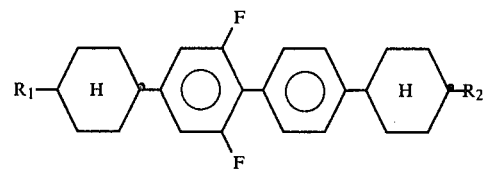

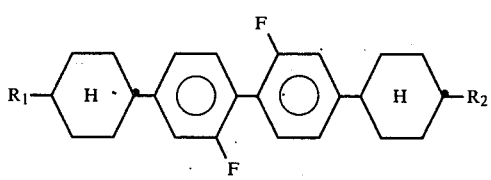

In these formulae, $R_1$ and $R_2$ are as defined for formula (I). The substituents in the 1- and 4-positions of the cyclohexane rings are always in the transarrangement; this is illustrated in the formula by the thickened black dot on the right-hand side of the cyclohexane rings.

Those compounds of formula (I) which are not covered by sub-formulae (Ia) and (Ic) have the same advantageous properties, but are more difficult to prepare and therefore less economical. The compounds of the sub-formulae (Ia) to (Ic) are therefore preferred.

In the compounds of formula (I), the alkyl or alkoxy radicals $R_1$ and $R_2$ can be straight-chain or branched. If they are straight-chain, i.e., methyl, ethyl, n-propyl, n-butyl, n-pentyl, n-hexyl, n-heptyl or n-octyl, or the corresponding alkoxy groups, the corresponding compounds as a rule, have higher clear points than the compounds with branched wing groups $R_1$ and/or $R_2$. For this reason, usually at most one of the wing groups $R_1$ and $R_2$ contains a branched carbon chain.

The compounds of formula (I) with a branched wing group $R_1$ or $R_2$ are occasionally important due to a higher solubility in the conventional liquid-crystalline base materials. In particular, they are important as chiral doping substances if they possess optical activity because of the chain branching. Such branched wing groups generally do not contain more than one chain branching. Those branched hydrocarbon radicals are preferred in which a methyl or ethyl group is present in the 1-position, 2-position or 3-position of a longer carbon chain, for example 2-methylpropyl, 2-methylbutyl, 3-methylbutyl, 2-methylpentyl, 3-methylpentyl, 2-ethylhexyl or 1-methylhexyl. The wing groups $R_1$ and $R_2$ together can contain up to 16 carbon atoms. Within the scope of the present invention, preferred are those in which $R_1$ and $R_2$ together contain 3 to 14, in particular 4 up to 12, carbon atoms. Preferably, at least one of the wing groups is an alkyl group.

The compounds of this invention are prepared by methods which are fully conventional for substances of this type. In a preferred process, compounds of formula (II)

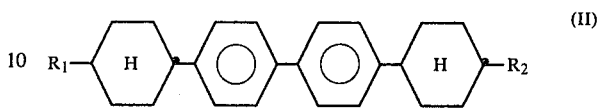

wherein $R_1$ and $R_2$ are as defined for formula (I), are treated with a nitrating agent. The mononitro- and dinitro-4,4'-bis-(cyclohexyl)-biphenyls thus formed, in a manner again conventional per se, are separated off and reduced to the corresponding monoamino and diamino compounds. These amino compounds are conventionally diazotised; converted by reaction with a fluoborate into the corresponding diazonium fluorborates; and, from the latter, fluorine-containing 4,4'-bis-(cyclohexyl)-biphenyls of formula (I) are prepared by thermal decomposition. Any mixtures of monofluoro and difluoro compounds or isomers thus obtained are then separated in conventional manner for example by fractional crystallization, extraction or by a chromatographic method. Of course, such a separation can be carried out previously at one of the preceding synthesis steps, for example after the nitration or subsequent to the reduction or the preparation of the diazonium tetrafluoborates.

The nitration of the starting materials of the formula (II) is carried out in a manner known per se, for example with a mixture of sulfuric acid and nitric acid, with acetic acid/nitric acid, or with an acyl nitrate, such as benzoyl nitrate or acetyl nitrate. The distribution of isomers in the resulting mixture of nitration products can be influenced in the direction of the main desired products by a suitable selection of the nitration conditions which are known per se from the literature, for example the nature and concentration of the nitrating agent, the solvent, the temperature, the duration of the reaction and/or the catalyst. The reduction of the nitro compounds to the amino compounds is carried out by standard methods, for example by catalytic hydrogenation or by treatment with sodium sulfide, with aqueous dithionite or with tin(II) chloride and hydrochloric acid.

The diazotisation, conversion to the diazonium tetrafluoborate and thermal decomposition (Schiemann-Balz synthesis) are likewise carried out in a manner known per se, for example according to one of the process variants described in "Organic Reactions," volume 5 (1949), pages 193–228.

In another synthesis process, the starting material used is a 4-bromobiphenyl which is monosubstituted or disubstituted by fluorine. This starting material is reacted successively with magnesium, a 4-alkylcyclohexanone or 4-alkoxycyclohexanone and an acid. The 4-[4-alkyl- or -alkoxycyclohexen-1-yl]-mono- or -di-fluorobiphenyl thus obtained is then hydrogenated to the 4-(4-alkyl- or -alkoxycyclohexyl)-mono- or -difluorobiphenyl. This intermediate is brominated and the bromine atom in the resulting 4'-bromo-4-(4-alkyl- or -alkoxycyclohexyl)-mono- or -di-fluorobiphenyl is exchanged for a 4-alkyl- or -alkoxycyclohexyl group in the manner described above. In place of the reaction with magnesium to form the intermediate Grignard compound, the bromine atoms in the intermediates can also be exchanged for the cyclohexyl groups by treatment with a metal-organic compound, for example butyllithium, and subsequent reaction with the cyclohexanone derivatives. If mixtures of cis-cyclohexyl and trans-cyclohexyl derivatives are obtained in this step, they can be converted in a manner conventional per se, for example by treatment with potassium tert-butylate in dimethylformamide, into the transcompounds which are thermodynamically more stable. Fractions of the undesired cis-isomers which may still be contained in the equilibrium mixture can then be separated off by fractional crystallization or by chromatographic methods.

The starting materials of formula (II) are all known compounds or can be conventionally prepared from known compounds. They are described in, e.g., German Offenlegungsschrift No. 2,948,836.

The dielectrics of this invention comprise 2 to 15, preferably 3 to 12, components of which at least one is a fluorine-containing 4,4'-bis-(cyclohexyl)-biphenyl derivative of formula (I). The other constituents are selected from among nematic or nematogenic substances from the group comprising the classes of azoxybenzenes, benzylideneanilines, biphenyls, terphenyls, phenyl or cyclohexyl benzoates, phenyl or cyclohexyl cyclohexanecarboxylates, phenylcyclohexanes, cyclohexylbiphenyls, cyclohexylcyclohexanes, cyclohexylnaphthalenes, 1,4-bis-cyclohexylbenzenes, 4,4'-bis-cyclohexylbiphenyls, phenyl- or cyclohexylpyrimidines, phenyl- or cyclohexyl-dioxanes, stilbenes which may be halogenated, benzyl phenyl ethers, tolanes and substituted cinnamic acids. The most important compounds which can be used as constituents of liquid-crystalline dielectrics of this type can be characterized by the formula (III)

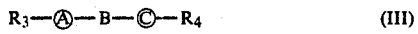     (III)

wherein A and C are each a carbocyclic or heterocyclic ring system selected from the group comprising 1,4-disubstituted benzene rings and cyclohexane rings, 4,4'-disubstituted biphenyl, phenylcyclohexane and cyclohexyl-cyclohexane systems, 2,5-disubstituted pyrimidine rings and 1,3-dioxane rings, 2,6-disubstituted naphthalene, dihydro- and tetrahydronaphthalene, quinazoline and tetrahydroquinazoline; B is

| | |
|---|---|
| —CH=CH— | —N(O)=N— |
| —CH=CY— | —CH=N(O)— |
| —C≡C— | —CH$_2$—CH$_2$— |
| —CO—O— | —CH$_2$—O— |
| —CO—S— | —CH$_2$—S— |
| —CH=N— | |

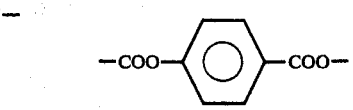

or a C—C single bond; Y is halogen, preferably chlorine, or —CH; and $R_3$ and $R_4$ are alkyl, alkoxy, alkanoyloxy or alkoxycarbonyloxy each of up to 18, preferably up to 8, carbon atoms, or one of these radicals can also be —CN, —NC, —NO$_2$, —CF$_3$, F, Cl or Br. In most of these compounds, $R_3$ and $R_4$ are different from one another, one of these radicals being an alkyl group or an alkoxy group in most cases. Other variants of the envisaged substituents, however, are also common. Many such substances, or mixtures thereof, are commercially available.

The dielectrics of this invention contain, as a rule, at least 30, preferably 50–99, in particular 60–98, percent by weight of the compounds of formulas (I) and (III). Of this, preferably at least 5 percent by weight, and in most cases even 10 or more percent by weight, are made up by one or more compounds of formula (I). However, this invention also comprises those liquid-crystalline dielectrics to which only less than 5 percent by weight, for example 0.1 to 3 percent by weight, of one or more compounds of formula (I) has been added, for example for doping purposes. On the other hand, the compounds of formula (I) can account for up to 60 percent by weight of the dielectrics of this invention. Preferably, the liquid-crystalline dielectrics of this invention contain 10 to 30 percent by weight of one or more compounds of the formula (I).

The preparation of the dielectrics of this invention is carried out in a manner conventional per se. As a rule, the desired amount of the components used in a smaller quantity is dissolved in the component representing the main constituent, advantageously at an elevated temperature. If a temperature above the clear point of the main constituent is chosen for this, the completeness of the solution process can be observed with particular ease.

The liquid-crystalline dielectrics of this invention can be modified by suitable additives in such a way that they can be used in all hitherto disclosed types of liquid crystal display elements. Additives of this type are known to those skilled in the art and are extensively described in the relevant literature. For example, it is possible to add dichroic dyes or substances which are intended to modify the dielectric anisotropy, the viscosity, the conductivity and/or the orientation of the nematic phases. Substances of this type are described, for example, in German Offenlegungsschriften Nos. 2,209,127; 2,240,864; 2,321,632; 2,338,281; 2,450,088; 2,637,430; 2,853,728 and 2,902,177, all of which are incorporated by reference herein.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

In the examples, m.p. denotes the melting point, and c.p. denotes the clear point of a liquid-crystalline substance in degrees centigrade; boiling points are marked b.p.

EXAMPLE 1

(a) 45.8 g of 4,4'-bis-(trans-4-n-pentylcyclohexyl)-biphenyl is introduced into a warm mixture, at 40°, of 20 ml of 65% nitric acid and 24 ml of 96% sulfuric acid. After the end of the addition, the reaction mixture is stirred for 1 further hour at 60° and is poured onto 300 g of ice. The 4,4'-bis-(trans-4-n-pentylcyclohexyl)-2-nitrobiphenyl which has crystallized out is filtered off and recrystallized from ethanol.

(b) 20 g of 4,4'-bis-(trans-4-n-pentylcyclohexyl)-2-nitrobiphenyl is dissolved in 150 ml of tetrahydrofuran. After 3 g of palladium-on-carbon (10% of Pd) has been added, hydrogen is passed into the mixture for 1 hour under normal pressure and at room temperature. The catalyst is then filtered off and the filtrate is evaporated. The remaining 4,4'-bis-(trans-4-n-pentylcyclohexyl)-2-aminobiphenyl is recrystallized from petroleum ether (boiling range 40°–60°).

(c) 15.0 g of 4,4'-bis-(trans-4-n-pentylcyclohexyl)-2-aminobiphenyl is suspended in 10 ml of 36% aqueous hydrochloric acid. After 10 ml of dioxane has been added, a solution of 3.8 g of sodium nitrite in 15 ml of water is added dropwise at 0° C. Immediately afterwards, and likewise at 0° C., a solution of 12 g of sodium tetrafluoborate in 20 ml of water is added dropwise. The precipitate which forms is filtered off after 30 minutes, washed with ice water and dried in vacuo at room temperature; and that dried powder of diazonium tetrafluoborate is heated to 120° C. until the evolution of gas ceases, and the remaining 4,4'-bis-(trans-4-n-pentylcyclohexyl)-2-fluorobiphenyl is recrystallized from ethanol.

The following are prepared analogously:
4,4'-bis-(trans-4-n-propylcyclohexyl)-2-fluorobiphenyl,
4-(trans-4-methylcyclohexyl)-4'-(trans-4-n-butylcyclohexyl-2-fluorobiphenyl,
4-(trans-4-ethylcyclohexyl)-4'-(trans-4-n-propylcyclohexyl)-2-fluorobiphenyl,
4-(trans-4-n-propylcyclohexyl)-4'-(trans-4-n-pentylcyclohexyl)-2-fluorobiphenyl,
4-(trans-4-n-pentylcyclohexyl)-4'-(trans-4-n-propylcyclohexyl)-2-fluorobiphenyl,
4-(trans-4-ethoxycyclohexyl)-4'-(trans-4-n-propylcyclohexyl)-2-fluorobiphenyl,
4-(trans-4-n-hexylcyclohexyl)-4'-(trans-4-n-butoxycyclohexyl)-2-fluorobiphenyl,
4-(trans-4n-heptylcyclohexyl)-4'-(trans-methylcyclohexyl)-2-fluorobiphenyl,
4-(trans-4-methoxycyclohexyl)-4'-[trans -4-(2-methylbutyl)-cyclohexyl)]-2-fluorobiphenyl,
4,4'-bis-(trans-4-n-butylcyclohexyl)-2-fluorobiphenyl,
4,4'-bis-(trans-4-ethylcyclohexyl)-2-fluorobiphenyl and
4,4'-bis-(trans-4-n-propylcyclohexyl)-2,5-difluorobiphenyl.

EXAMPLE 2

(a) A solution of 24.5 g of 4-(trans-4-n-pentylcyclohexyl)-aniline in 100 ml of toluene is treated successively with 35 ml of pyridine and then dropwise with a solution of 12 g of acetyl chloride in 25 ml of toluene. Subsequently, the reaction mixture is extracted by shaking with 100 ml of water, and the organic phase is separated off, dried over sodium sulfate and evaporated. 20 g of the acetyl-N-4-(trans-4-n-pentylcyclohexyl)-anilide which remains is introduced in portions of 1–2 g into a mixture of 118 ml of nitric acid (d=1.40) and 47 ml of sulfuric acid (d=1.84) in such a way that the temperature remains between 30° C. and 40°. After the end of the addition, the mixture is stirred for an additional 15 minutes and is then poured into 700 ml of cold water. The two-phase system is extracted with methylene chloride, after which the organic phase is freed from solvent by distillation. The residue is dissolved in 100 ml of boiling ethanol, a solution of 15 g of potassium hydroxide in 20 ml of water is then added and the mixture is heated under reflux for a further 20 minutes. After it has been poured into 500 ml of water, the mixture is again extracted with methylene chloride, the solvent is distilled off and the 4-(trans-4-n-pentylcyclohexyl)-2-nitroaniline which remains is purified by distillation under reduced pressure; b.p. $_{0.3}$ mbar 139°–143°.

(b) 12.0 g of 4-(trans-4-n-pentylcyclohexyl)-2-nitroaniline is suspended in 10 ml of 36% hydrochloric acid. After 10 ml of dioxane has been added, a solution of 2.8 g of sodium nitrite in 6 ml of water is added dropwise at 0° C. With vigorous stirring, a solution of 4.5 g of copper(I) chloride in 17 ml of 36% hydrochloric acid is then allowed to run in. After stirring for 1 hour, the reaction mixture is warmed to room temperature, poured into 200 ml of water and extracted with methylene chloride. The organic phase is dried over calcium chloride and evaporated, and the 4,4'-bis-(trans-4-n-pentylcyclohexyl)-2,2'-dinitrobiphenyl which remains is recrystallized from ethanol.

(c) 2 g of palladium-on-carbon (10% of Pd) is added to a solution of 7.5 g of 4,4'-(trans-4-n-pentylcyclohexyl)-2,2'-dinitrobiphenyl in 100 ml of tetrahydrofuran, and hydrogen is passed into this suspension for 1 hour at room temperature. The catalyst is then filtered off and the filtrate is evaporated. 4.0 g of the 4,4'-bis-(trans-4-n-pentylcyclohexyl)-2,2'-diaminobiphenyl which remains is suspended in 15 ml of 26% aqueous tetrafluoboric acid. After 5 ml of dioxane has been added, a solution of 1.2 g of sodium nitrite in 6 ml of water is added dropwise at 0° C. The precipitate which forms is filtered off after 1–2 hours, washed with ice water and dried in vacuo at room temperature. The dried powder is heated to 120°. After the evolution of BF$_3$ has ceased, the 4,4'-bis-(trans-4-n-pentylcyclohexyl)-2,2'-difluorobiphenyl which remains is recrystallized.

The following are prepared analogously:
4,4'bis-(trans-4-n-ethylcyclohexyl)-2,2'-difluorobiphenyl,
4,4'-bis-(trans-4-n-propylcyclohexyl)-2,2'-difluorobiphenyl,
4,4'-bis-(trans-4-n-butylcyclohexyl)-2,2'-difluorobiphenyl,
4,4'-bis-(trans-4-n-hexylcyclohexyl)-2,2'-difluorobiphenyl and
4,4'-bis-(trans-4-ethoxycyclohexyl)-2,2'-difluorobiphenyl.

EXAMPLE 3

A liquid-crystalline mixture of
23.9% of 4-(trans-4-n-propylhexyl)-benzonitrile,
36.1% of 4-(trans-4-n-pentylcyclohexyl)-benzonitrile,
25.0% of 4-(trans-4-n-heptylcyclohexyl)-benzonitrile and
15.0% of 4-(trans-4-n-pentylcyclohexyl)-4'-cyanobiphenyl has a melting point of $-6°$, a clear point of $+70°$ and a viscosity of $29 \times 10^{-1}$ Pa.s at 20°.

A liquid-crystalline dielectric consisting of 90% of this mixture and 10% of 4,4'-bis-(trans-4-n-pentylcyclohexyl)-2-fluorobiphenyl has a melting point of $-15°$, a clear point of 86° and a viscosity of $27 \times 10^{-3}$ Pa.s at 20°.

EXAMPLE 4

A liquid-crystalline mixture of
21.1% of 4-(trans-4-ethylcyclohexyl)-benzonitrile,
22.2% of 4-(trans-4-n-butylcyclohexyl)-benzonitrile,
13.9% of 4-ethyl-4'-cyanobiphenyl, 17.8% of 4-n-butyl-4'-cyanobiphenyl, 16.1% of 4-(trans-4-n-pentylcyclohexyl)-4'-cyanobiphenyl and 8.9% of 4-n-pentyl-4''-cyano-p-terphenyl has a nematic phase in the temperature range from $-6°$ to $+64°$ and a viscosity of $32 \times 10^{-3}$ Pa.s at $20°$.

A liquid-crystalline dielectric consisting of 90% of this mixture and 10% of 4,4'-bis-(trans-4-n-pentylcyclohexyl)-2-fluorobiphenyl has a nematic phase in the widened temperature range from $-12°$ to $+80°$ and a viscosity of $33 \times 10^{-3}$ Pa.s at $20°$.

EXAMPLE 5

The liquid-crystalline mixture of 38.2% of 4-(trans-4-n-pentylcyclohexyl)-benzonitrile, 15.3% of 4-(trans-5-n-propyl-1,3-dioxan-2-yl)-benzonitrile, 15.9% of 4-(trans-5-n-pentyl-1,5-dioxan-2-yl)-benzonitrile, 18.8% of 4-(trans-5-n-hexyl-1,3-dioxan-2-yl)-benzonitrile and 11.8% of 4-(trans-4-n-pentylcyclohexyl)-4'-cyanobiphenyl has a nematic mesophase in the temperature range from $-5°$ to $+62°$ and a viscosity of $35 \times 10^{-3}$ Pa.s at $20°$.

A liquid-crystalline dielectric consisting of 85% of this mixture and 15% of 4,4'-bis-(trans-4-n-pentylcyclohexyl)-2-fluorobiphenyl has a nematic phase in the widened temperature range from $-15°$ to $+86°$ and a viscosity of $26 \times 10^{-3}$ Pa.s at $20°$.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of the formula

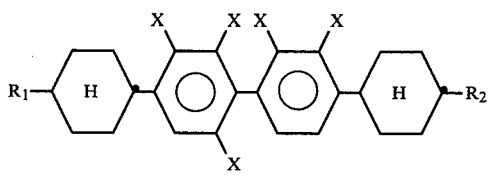

wherein $R_1$ and $R_2$ are identical or different and each is alkyl or alkoxy each of up to 8 C atoms, and one or two of the substituents X are fluorine and the others are hydrogen.

2. A compound of claim 1 of the formula

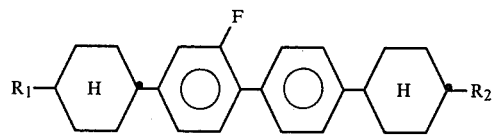

wherein $R_1$ and $R_2$ are identical or different and each is alkyl or alkoxy each of up to 8 C atoms.

3. A compound of claim 1 of the formula

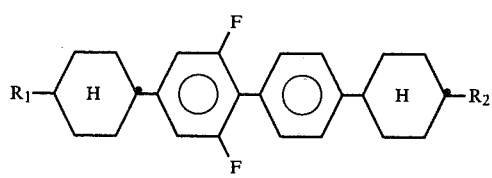

wherein $R_1$ and $R_2$ are identical or different and each is alkyl or alkoxy each of up to 8 C atoms.

4. A compound of claim 1 of the formula

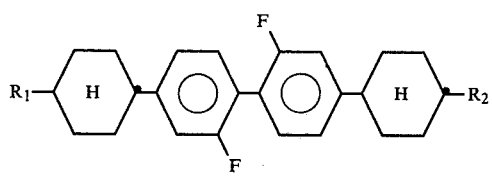

wherein $R_1$ and $R_2$ are identical or different and each is alkyl or alkoxy each of up to 8 C atoms.

5. A compound of claim 1 wherein $R_1$ and $R_2$ are straight chained.

6. A compound of claim 1 wherein one of $R_1$ and $R_2$ is straight chained and the other contains only one chain branching.

7. A liquid-crystalline dielectric useful in electro-optical display elements, which comprises at least two liquid-crystalline components, wherein at least one of these liquid-crystalline components is a 4,4'-dicyclohexylbiphenyl compound of claim 1.

8. A liquid crystalline dielectric of claim 7 wherein the amount of said 4,4'-dicyclohexylbiphenyl compound is 5–60% by weight.

9. A liquid crystalline dielectric of claim 7 wherein the amount of said 4,4'-dicyclohexylbiphenyl compound is 0.1 to less than 5% by weight.

10. In an electro-optical display element comprising a liquid crystal cell, an improvement wherein the liquid crystal cell comprises a dielectric of claim 7.

* * * * *